United States Patent [19]

Kenna

[11] Patent Number: 5,108,437
[45] Date of Patent: Apr. 28, 1992

[54] MODULAR PROSTHESIS

[75] Inventor: Robert V. Kenna, Hobe Sound, Fla.

[73] Assignee: Pfizer Hospital Products Group, Inc., New York, N.Y.

[21] Appl. No.: 244,446

[22] Filed: Sep. 14, 1988

[51] Int. Cl.⁵ .......................... A61F 2/30; A61F 2/36
[52] U.S. Cl. ........................................ 623/16; 623/23; 623/18
[58] Field of Search .................. 623/16, 18, 19, 20, 623/22, 23; 403/100, 354, 348

[56] References Cited

U.S. PATENT DOCUMENTS

| | | | |
|---|---|---|---|
| 2,062,108 | 11/1936 | Rickerson | 403/348 |
| 2,895,757 | 7/1959 | Kaspar | 403/100 |
| 3,243,165 | 3/1966 | Woody et al. | 403/348 |
| 4,607,974 | 8/1986 | Brothers et al. | 403/354 |
| 4,632,195 | 12/1986 | Emmerich | 403/348 |
| 4,676,797 | 6/1987 | Anapliotis et al. | 623/23 |
| 4,768,258 | 9/1988 | Langenstein | 403/348 |
| 4,787,907 | 11/1988 | Carignan . | |
| 4,790,854 | 12/1988 | Harder et al. | 623/23 |
| 4,822,370 | 4/1989 | Schelhas | 623/22 |

FOREIGN PATENT DOCUMENTS

| | | |
|---|---|---|
| 0201442 | 4/1985 | European Pat. Off. . |
| 0145641 | 6/1985 | European Pat. Off. . |
| 0163121 | 12/1985 | European Pat. Off. . |
| 0212192A1 | 3/1987 | European Pat. Off. . |
| 0243298A2 | 10/1987 | European Pat. Off. . |
| 0257359 | 3/1988 | European Pat. Off. . |
| 0145641A1 | 6/1988 | European Pat. Off. . |
| 2454181A1 | 5/1976 | Fed. Rep. of Germany . |
| 8306663U1 | 9/1986 | Fed. Rep. of Germany . |
| 3138848C2 | 2/1987 | Fed. Rep. of Germany . |
| 3336005A1 | 9/1987 | Fed. Rep. of Germany . |
| 3605630 | 9/1987 | Fed. Rep. of Germany ........ 623/16 |
| 2070939 | 9/1981 | United Kingdom . |

Primary Examiner—David Isabella
Attorney, Agent, or Firm—Peter C. Richardson; Lawrence C. Akers; Elizabeth O. Slade

[57] ABSTRACT

A modular prosthesis features at least one male-female fitting, with the female portion being located on one end of one segment of that prosthesis and the mating male portion being located on one end of a second prosthesis segment, with at least the proximal part of the male-female fitting having a taper. The two parts of that fitting can be locked together by a locking mechanism in the form of a novel spacer which also has a taper which mates with the taper of the male-female fitting described above. Multiple modular segments can be assembled together so as to produce a prosthesis as required by the patient.

13 Claims, 3 Drawing Sheets

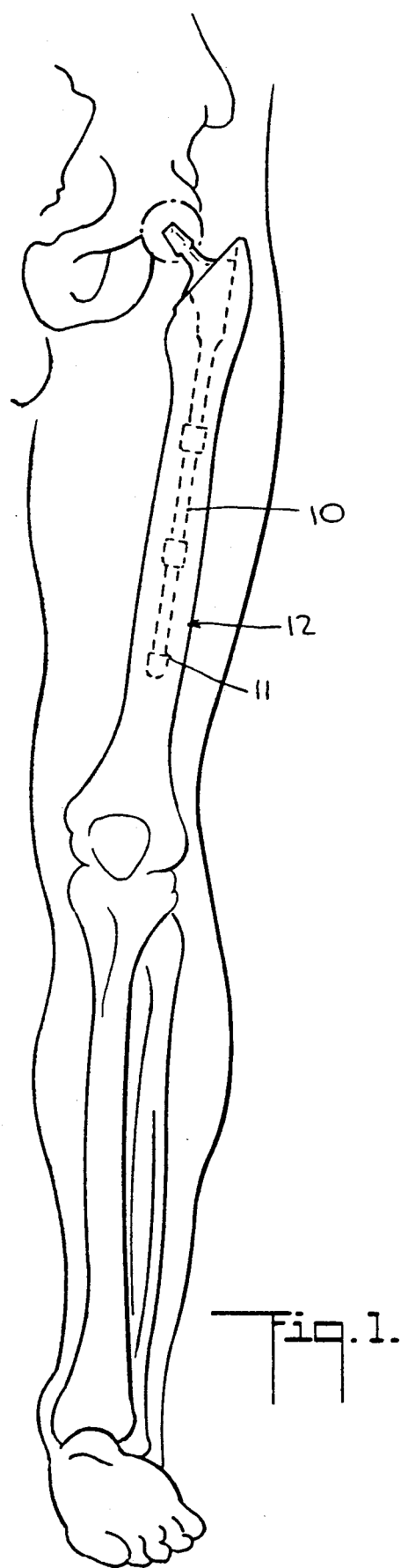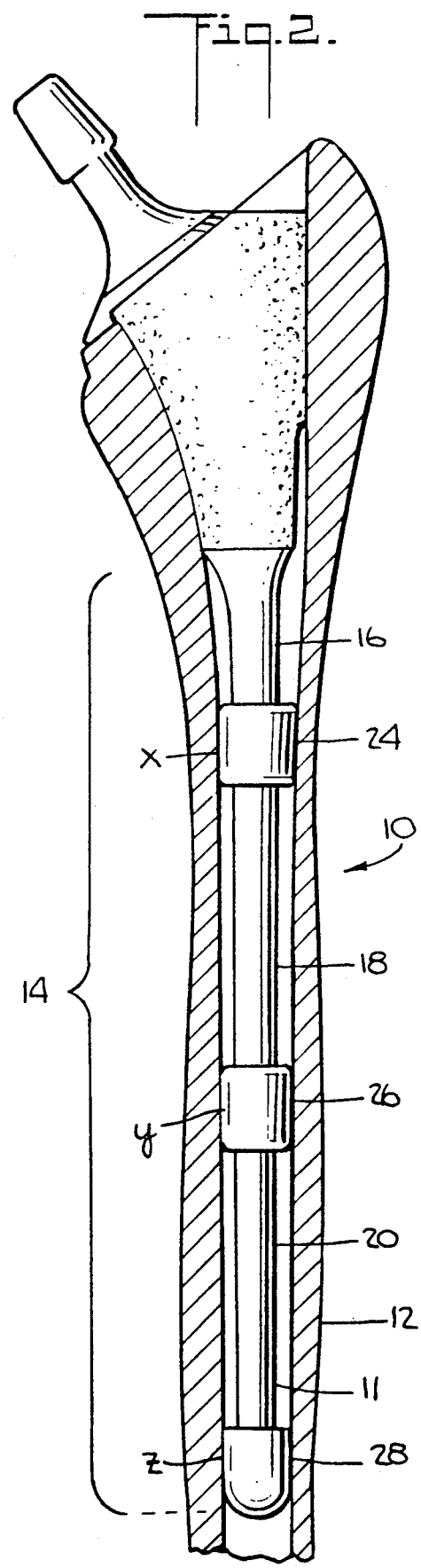

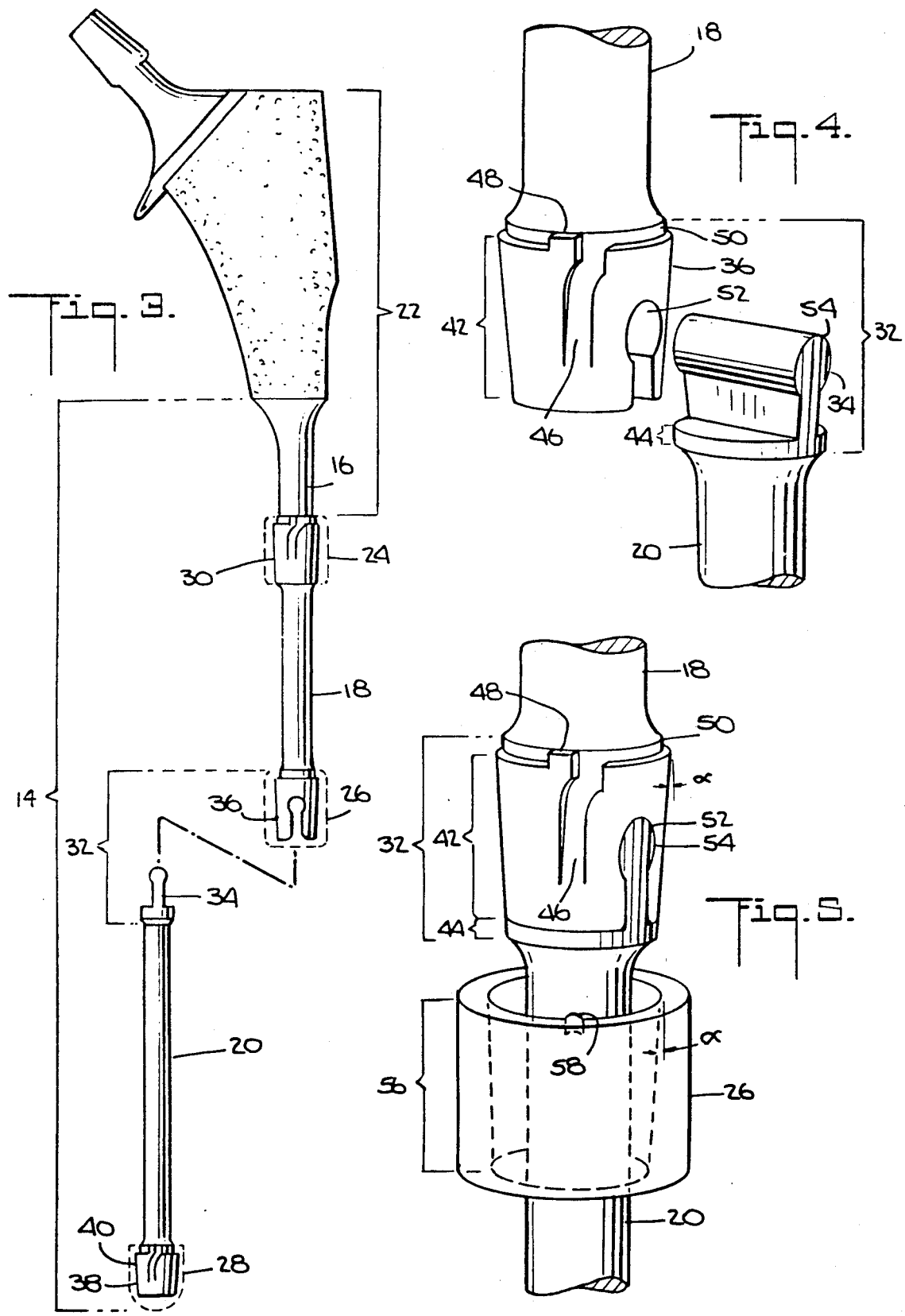

MODULAR PROSTHESIS

BACKGROUND OF THE INVENTION

This invention relates generally to modular prostheses and relates more particularly to modular femoral hip prostheses.

In the field of orthopedics, modular prostheses have been known. See for example, U.S. Pat. No. 4,728,333 to Masse et al. and European Patent Application 0257359, to Bolesky et al., which relate to modular hip prostheses.

Modular prostheses have the advantage that the number of stock items necessary for fitting the general population of patients requiring prostheses can be reduced, as compared with non-modular prostheses.

A goal in fitting a hip prosthesis to a patient is to provide the patient with a prosthesis which has a modulus of elasticity which is compatible to that of the bone of the patient. Additionally, it is desirable to have the hip implant precisely fit the intramedullary femoral canal of the patient requiring the hip implant.

An object of this invention is a modular prosthesis which can be assembled from a minimum number of shelf stock modular items and which will fit the bone of an individual patient quite precisely.

Another object of this invention is a femoral hip implant having a modulus of elasticity compatible to the modulus of elasticity of the bone of an individual patient.

Yet another object of this invention is a modular femoral hip prosthesis which can be made either from metal or from composite materials and which will have a modulus of elasticity compatible to the modulus of elasticity of the femur bone of an individual patient.

SUMMARY OF THE INVENTION

According to the invention, a modular prosthesis comprises a male fitting located on one end of one prosthesis segment, together with a mating female fitting located on one end of a second prosthesis segment, at least one of which two fittings has a taper. In a preferred embodiment, included also is a novel spacer which also has a tapered surface on its inner diameter such that it mates with the taper of the male-female fitting.

In a preferred embodiment, a modular femoral hip prosthesis is provided which very precisely fits an intramedullary canal of the femur of the patient requiring a hip implant. In this embodiment, two stem segments are connected together by use of a male-female fitting, which has a taper. The spacer fits onto and mates with at least the proximal-most portion of the male-female fitting. In a preferred embodiment, that male-female fitting has a groove which, together with a key located within the spacer, provides a locking mechanism which prevents the modular prosthesis from becoming disassembled either during or after insertion into the body of the patient.

Also according to the invention, a method for producing a modular prosthesis which has a modulus of elasticity very compatible to that of the bone of the patient and which fits very closely within an intramedullary of the patient is provided. In a preferred embodiment, a method for producing a modular femoral hip prosthesis is given.

Further, according to the invention, a spacer having a tapered inner diameter which is suitable for mating with a male-female fitting joining two portions of a modular prosthesis is given. In a preferred embodiment, that spacer has a key which connects and locks together the two prosthesis portions to be connected.

BRIEF DESCRIPTION OF THE DRAWINGS

FIG. 1 is a schematic illustration, showing implanted within an intramedullary canal of a left femur of a patient a modular femoral hip prosthesis which is a preferred embodiment according to the invention.

FIG. 2 is a cross-sectional enlarged view of the embodiment shown in FIG. 1.

FIG. 3 is a pictorial view of the embodiment of the invention shown in FIG. 2, exhibiting a preferred embodiment of a male-female fitting which has been disassembled so as to show its structure, with the dotted lines indicating spacers, one spacer being preferably positioned over each male-female fitting and one spacer also preferably positioned over the distal end of the final segment.

FIG. 4 is a pictorial view of the disassembled male-female fitting shown in FIG. 3, the female portion being located at the distal end of the proximal stem segment and the male portion being located at the proximal end of another stem segment.

FIG. 5 is a pictorial view of the male-female fitting of FIG. 4 shown in assembled position, with a spacer positioned below the fitting at a point in time when the spacer is about to be placed into contact with the fitting by moving the spacer upwards toward the assembled fitting, with the inwardly directed key on the spacer located just below a groove on the assembled fitting.

DETAILED DESCRIPTION OF THE DRAWINGS

Figure 6:
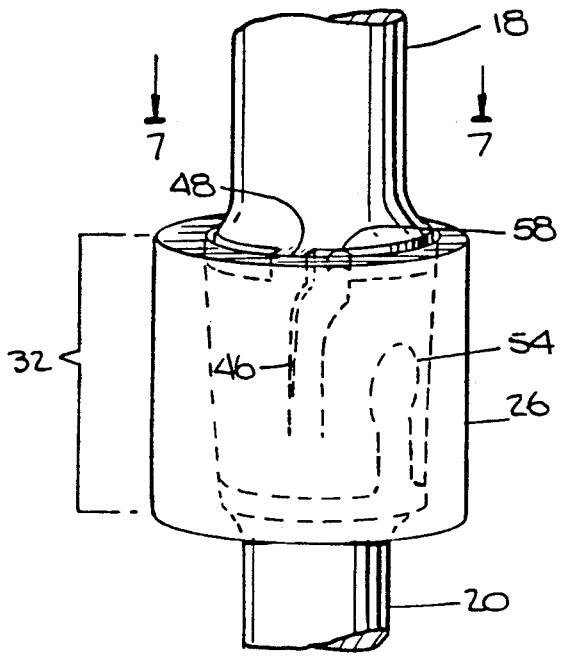
FIG. 6 is a pictorial view of the spacer and fitting shown in FIG. 5, in assembled position, with the key of the spacer located at the top of the groove.

In FIG. 1 is shown a preferred embodiment according to the invention of a modular femoral hip prosthesis, referred to generally as 10 and implanted within an intramedullary canal 11 of a left femur 12 of a patient.

As shown in greater detail in FIG. 2, in this preferred embodiment, modular femoral hip prosthesis 10 has a stem 14 made up of three segments, a proximal stem portion 16, an intermediate stem portion 18, and a distal stem portion 20. Proximal stem portion 16 is shown as an integral part of the main body portion 22 of the prosthesis. Proximal spacer 24 is shown in FIG. 2 at the intersection x of proximal stem portion 16 and intermediate stem portion 18. Intermediate spacer 26 is shown located within the intramedullary canal 11 at the intersection y between the intermediate stem portion 18 and the distal stem portion 20. And distal spacer 28 is shown within the intramedullary canal 11 located at position z at the lower extremity of distal stem portion 20. Male-female fittings (not shown in FIG. Z) are positioned within spacers 24 and 26, and a female portion is positioned within spacer 28.

In FIG. 3, spacers 24, 26, and 28 are shown in dotted lines, with proximal spacer 24 encompassing proximal male-female fitting 30, intermediate spacer 26 encompassing intermediate male-female fitting 32 (shown separated for clarity so as to demonstrate its component parts, which are male portion 34 and female portion 36), and distal spacer 28 encompassing distal fitting 38 (which in this embodiment is a female portion 40).

In FIG. 4, shown in larger detail is intermediate fitting 32, which comprises male portion 34 and female portion 36. Female portion 36 has a tapered portion 42 and male portion 34 has a tapered portion 44, which tapered portions preferably are tapered at the same angle $\alpha$. Female portion 36 has a groove 46 located therein, which preferably is located along a substantially straight line lying in a substantially distal-proximal direction. At the top of groove 46, on one side thereof is a stop 48 and at the other side thereof is a cutaway portion 50, which extends from groove 46 to stop 48, through an angle of nearly 360°. Also located within female portion 36 is a keyway 52, extending therethrough and into which key portion 54 can pass and fit securely therein. Stem portion 18 is shown integral with female portion 36, and stem portion 20 is shown integral with male portion 34. Key portion 54 is also tapered so that when it is inserted into keyway 52, a smoothly tapered assembled unit is formed. Keyway 52 is spaced apart from groove 46, preferably by an angle of about 90°.

In FIG. 5, key portion 54 is shown assembled within keyway 52. Other parts described previously are also shown in FIG. 5. Located below intermediate fitting 32 (which is shown in its assembled configuration) is intermediate spacer 26, shown at a point in time just prior to being assembled into locking position with intermediate fitting 32. Spacer 26 has a tapered portion 56, which is tapered preferably at the same angle as both tapered portion 42 and tapered portion 44 and which preferably has the same length as their combined length. Spacer 26 has an inwardly extending key 58, which will fit within groove 46 of intermediate fitting 32 and which will pass along cutaway portion 50 as spacer 26 is turned through nearly 360° until key 58 abuts stop 48. This provides a locking mechanism so that fitting 32 does not accidentally become separated into its component parts.

In FIG. 6, spacer 26 is shown in an assembled but unlocked position.

Figure 7:
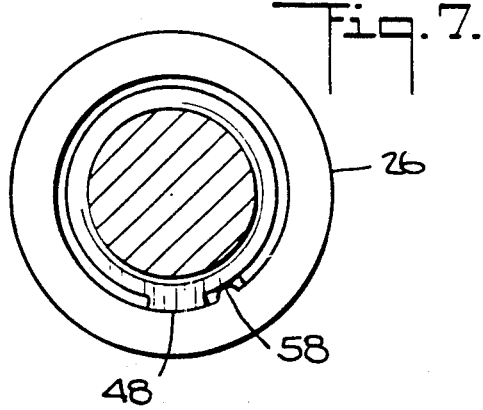
FIG. 7 is a cross-sectional view, taken along the line 7—7 shown in FIG. 6 as viewed downwardly in the distal direction, with the key located at the top of the groove in unlocked position.

In FIG. 7, in cross-section, inwardly extending key 58 is shown at the top of groove 46 in a position open and unlocked with respect to fitting 32.

Figure 8:
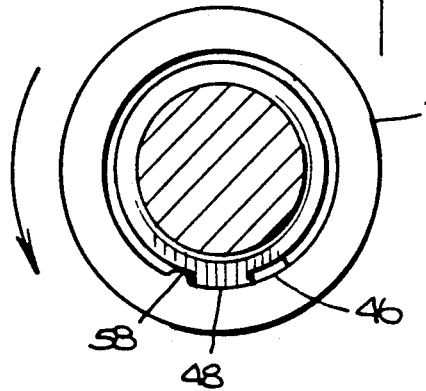
FIG. 8 is a cross-sectional view of the portion of the device shown in FIG. 7, with the key shown in its locked position (after the key has been rotated in a counterclockwise direction as indicated by the arrow through an angle of nearly 360° with respect to the position shown in FIG. 7).

In FIG. 8, inwardly extending key 58 is shown abutting groove 48, at a point in time after key 58 (and spacer 26) have been rotated through nearly 360°.

Figure 9:
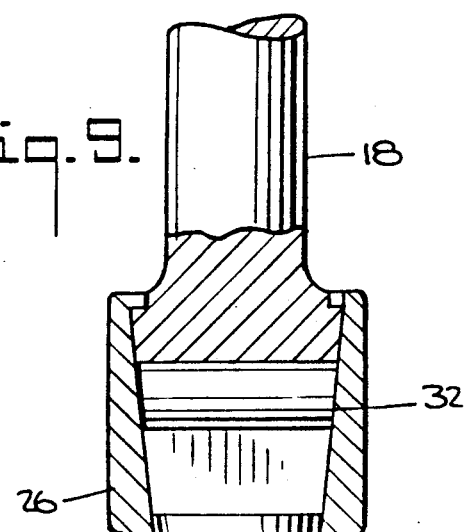
FIG. 9 is a pictorial view of the intermediate and distal fittings and the intermediate and distal spacers shown in FIG. 2, the intermediate fitting being shown in cross-section so as to exhibit the keyway hole.

In FIG. 9, intermediate fitting 32 is shown in an assembled position, with spacer 26 encompassing intermediate fitting 32. Distal spacer 28 is shown encompassing distal fitting 38 which is formed from female portion 40, without a male portion present.

In the practice of the invention, a preferred modular prosthesis comprises (1) a male fitting located on one end of one prosthesis segment, (2) a mating female fitting located on one end of a second prosthesis segment, with at least the proximal of the male and female fittings having a tapered portion, and (3) a spacer having a tapered surface on its inner diameter such that tapered surface mates with the tapered surface of the male-female fitting. Preferably the prosthesis will be a hip prosthesis, although the combination of the tapered male-female fitting and preferably with the spacer are suitable for other prostheses.

In the modular prosthesis of the invention, the number of prosthesis segments to be joined will be at least two prosthesis segments. Preferably these two segments will be stem sections, one of which can be (if desired), integral with the main body of the prosthesis device.

In the device of the invention, the joined stem segments can have smaller cross-sections than are normally found in femoral hip prosthesis stems. This makes it possible to obtain a prosthesis having a modulus of elasticity comparable to that of bone. Additionally, increased flexibility of the stem of the prosthesis is obtained.

In a preferred embodiment, three modular stem segments are connected. Modular stem portions can be mass produced for inter-connection, with a male fitting at one end and a female fitting at the other end. In connecting the stems, one free stem end will remain which can be either male or female (provided only that the tapered portions are tapered as described below).

In the practice of the invention, preferably there will be a tapered portion located on both a male-female fitting and on a spacer which mates with that assembled male-female fitting; and the tapered portion of that male-female fitting and the spacer will be substantially the same.

If more than one male-female fitting is used in assembling the modular device, the largest diameter fitting will be located at the proximal fitting; the next largest diameter fitting will be located adjacent thereto, and so forth. This is important for assembling the device. The tapered portions must be such that the spacer which fits at the proximal fitting must pass over the intermediate and distal fittings and the spacer which fits at the intermediate fitting must pass over the distal fitting.

Spacers are used so as to locate the segments of the device within the bone canal. Spacers are also used in the practice of the invention for locking male-female fittings together so that they cannot accidentally become dislodged.

In the practice of the invention, generally at least one spacer will be used. However, if the prosthetic device fits very tightly into the intramedullary canal concerned, it is possible that no spacer need be used.

Generally, one spacer will be used for each male-female fitting combination. Additionally, if desired, the terminal end of the prosthesis can have a spacer attached and locked thereto.

The largest inner diameters of the spacers will generally vary in the practice of the invention. The largest inner diameter of the proximal spacer will be greater than the largest inner diameter of the intermediate spacer, and the largest inner diameter of the distal spacer will be smaller than the largest diameter of either the proximal spacer or the intermediate spacer.

The outer diameters of the spacers have few requirements. The outer surface of a spacer can be shaped in the form of a cylinder, is desired. Alternatively, the outer surface of that spacer can have a slight taper if desired, or other alternatives can be contemplated. Additionally, if a series of spacers are used, the outer diameters of the series of spacers can all be the same. if desired. Alternatively, the proximal spacer might, if desired, have a slightly larger outer diameter than the other spacers used. The spacers to be used with the fittings will each have an inwardly directed key located at or near the proximal end of each spacer which will mate with a groove located within the proximal portion of the male-female fitting to which it is being assembled and locked.

A groove into which the spacer key will mate is located on the proximal portion of the male-female fitting. That proximal portion can be either a male or a female fitting. However, it is required that the largest diameter of the fitting be located (when it is assembled) at the proximal end of the male-female fitting.

A safety mechanism in a preferred embodiment of the device of the invention is formed from the key on a spacer and a stop located adjacent to the groove described above. When the key is inserted into the groove and the spacer is rotated through an angle of about 360°, the device does not easily become separated into its component parts.

The procedure for assembling the modular prosthesis according to the invention includes the following steps. The intramedullary canal of the patient will be reamed with a reamer having a particular diameter d. From a supply of right and left hip prosthesis body portions, one selects a suitable body portion for the patient. If that selected body portion has a stem portion which is integral with that body portion, that integral stem portion should have a diameter d and should have either a male or female fitting. Next, an additional stem portion is selected such that it has a proximal end having a female or male fitting, respectively, of which the largest diameter is d and a distal end having a male or female fitting, respectively, of which the largest diameter is d' wherein d is greater than d'. The male-female fittings have mating parts and each fitting has a tapered portion, with the largest diameter of the taper located proximally with respect to the smallest diameter of that taper.

A spacer is selected which has a largest inner diameter d and a tapered inner portion which mates with the tapered portion of the proximal male-female fitting; and if no additional stem portion is required, that spacer having diameter d will be passed over the distal stem end having diameter d' and over a tapered portion (as described above) which permits this passage of the spacer. The spacer then will be moved upwardly (i.e., proximally) so as to contact the intersection of the proximal stem portion and the additional stem portion at the proximal male-female fitting. Next that proximal spacer is rotated so as to lock that spacer in place at the junction of the first stem portion and second stem portion.

If it is desired to use more than two stem portions in the patient, additional segments can be selected so that the proximal-most spacer can be passed over all fittings except for the proximal fitting. The next spacer is passed over any distal fitting which is present and then is assembled onto the intermediate male-female fitting. A distal spacer can, if desired, be attached to the distal end of the distal stem segment.

I claim:

1. A modular prosthesis adapted to be inserted into bone and comprising at least a first stem portion having a distal end and a second stem portion having a distal end and a proximal end, said distal end of said first stem portion being joinable without threading to said proximal end of said second stem portion at a first junction and including also a first spacer which is adapted to contact bone and which fits over and locks with said first junction, wherein said modular prosthesis is a modular femoral hip prosthesis and wherein a first item selected from the group consisting of said distal end of said first stem portion and said proximal end of said second stem portion is a male dovetail portion having a first taper and a second item different from said first item selected from the group consisting of said distal end of said first stem portion and said proximal end of said second stem portion is a mating female dovetail portion having a second taper, wherein said first taper and said second taper are tapered at substantially the same angle.

2. A device according to claim 1 and including also a third stem portion having a distal end and a proximal end, wherein the proximal end of said third portion is joinable without threading to said distal end of said second portion at a second junction and including also a second spacer which fits over and locks with said second junction.

3. A device according to claim 2, wherein said second junction comprises a male dovetail portion having a third taper and a mating female dovetail portion having a fourth taper, wherein said third taper and said fourth taper are tapered at substantially the same angle.

4. A device according to claim 3, wherein said first spacer has an inner surface which is tapered so as to mate with said first taper.

5. A device according to claim 4, wherein said second spacer has an inner surface which is tapered so as to mate with said third taper.

6. A device according to claim 1 wherein said spacer has a locking mechanism which comprises a first inwardly directed key-like structure located on the interior surface of said first spacer and which can be inserted into a first keyway located within said first junction so as to lock said male dovetail portion and said female dovetail portion of said first junction together.

7. A device according to claim 6, wherein the distal end of said first keyway is spaced apart from said first male-female junction by an angle of about 90°.

8. A device according to claim 5, and including also a second locking mechanism which comprises a second key-like structure which is located on the interior surface of said second spacer and which can be inserted into a second keyway located within said second junction so as to lock said male dovetail portion and said female dovetail portion of said second junction together.

9. A device according to claim 8, wherein said distal end of said second keyway is spaced apart from said second male-female junction by an angle of about 90°.

10. A device according to claim 9 and including also a third spacer which is located at the distal end of said third portion.

11. A device according to claim 10, wherein said third spacer has a taper which mates with the taper of the distal end of said third portion.

12. A device according to claim 2, and including also a third spacer which is positioned at the distal end of said third portion.

13. A modular prosthesis adapted to be inserted into bone and comprising at least a first stem portion having a distal end and a second stem portion having a distal end and a proximal end, said distal end of said first stem portion being joinable without threading to said proximal end of said second stem portion at a first junction and including also a first spacer which is adapted to contact bone and which fits over and locks with said first junction, wherein said distal end of said first stem portion is joinable to said proximal end of said second stem portion by means of a dovetail connection.

* * * * *